United States Patent [19]
Ruggeri

[11] Patent Number: 5,871,699
[45] Date of Patent: Feb. 16, 1999

[54] APPARATUS AND METHOD FOR DRAWING LIQUID SAMPLES AND DISPENSING THEM INTO A PLURALITY OF TEST TUBES

[76] Inventor: Guido Ruggeri, Ducal 8-9, Marina Baie des Anges, F-06270 Villeneuve Loubet, France

[21] Appl. No.: 860,475

[22] PCT Filed: Jan. 9, 1996

[86] PCT No.: PCT/EP96/00052

§ 371 Date: Jun. 26, 1997

§ 102(e) Date: Jun. 26, 1997

[87] PCT Pub. No.: WO96/21853

PCT Pub. Date: Jul. 18, 1996

[30] Foreign Application Priority Data

Jan. 10, 1995 [IT] Italy ................................ MI95A0022

[51] Int. Cl.[6] ................................ G01N 1/14; A61B 5/14
[52] U.S. Cl. ........................... 422/100; 422/99; 422/103; 436/180; 600/575; 600/579
[58] Field of Search ..................................... 600/575, 576, 600/577, 578, 579; 422/99, 100, 103, 104; 436/180

[56] References Cited

U.S. PATENT DOCUMENTS

| | | |
|---|---|---|
| 3,405,706 | 10/1968 | Cinqualbre .............................. 600/575 |
| 3,848,581 | 11/1974 | Cinqualbre et al. ..................... 600/575 |
| 4,569,236 | 2/1986 | Kitchen et al. ...................... 600/575 X |
| 4,649,967 | 3/1987 | Gruenstein et al. ....................... 141/59 |
| 4,676,256 | 6/1987 | Golden ..................................... 600/575 |
| 4,784,157 | 11/1988 | Halls et al. .............................. 600/575 |
| 4,999,307 | 3/1991 | Oakley .................................... 600/575 |
| 5,084,034 | 1/1992 | Zanotti ................................ 600/575 X |
| 5,110,557 | 5/1992 | Brown et al. ........................... 422/101 |

FOREIGN PATENT DOCUMENTS 0 107 579 5/1984 European Pat. Off. .
1247657 10/1960 France .

*Primary Examiner*—Harold Y. Pyon
*Attorney, Agent, or Firm*—R. Neil Sudol; Henry D. Coleman

[57] ABSTRACT

An apparatus including a drawing element, a plurality of test tubes with airtight pierceable caps and a sucking system, suitably connected through ducts which are at least partially embodied in a disposable linking element, so that while preprogrammed volumes of air are orderly sucked out of said test tubes, programmed quantities of sample are collected into each of them. Some different construction patterns at different technological levels and an embodiment of said apparatus are outlined. A method for using it is described.

17 Claims, 9 Drawing Sheets

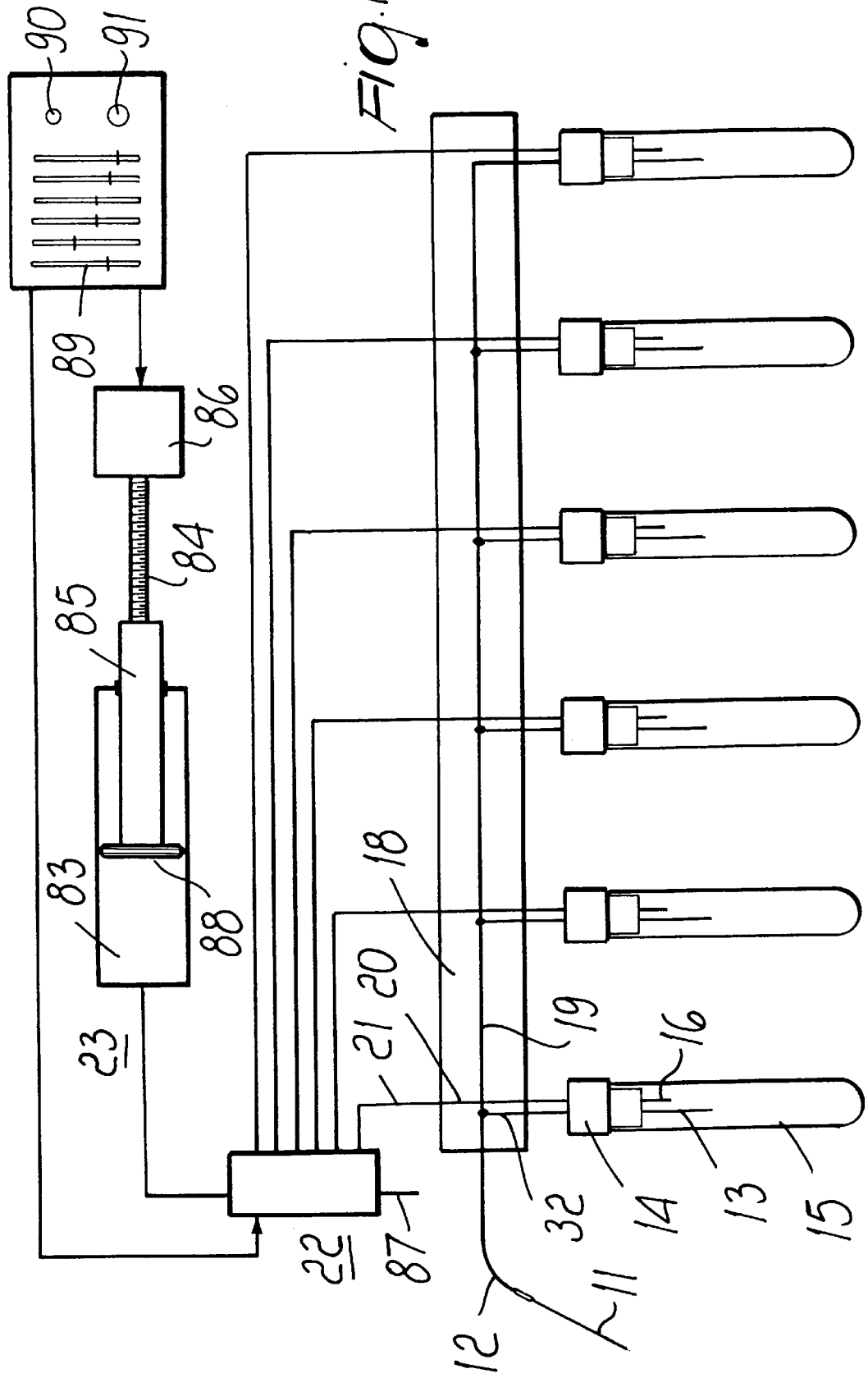

APPARATUS AND METHOD FOR DRAWING LIQUID SAMPLES AND DISPENSING THEM INTO A PLURALITY OF TEST TUBES

This application is a 371 of PCT/EP96/00052 filed on Jan. 9, 1996.

BACKGROUND OF THE INVENTION

1. Field of the Invention

This invention relates to an apparatus and method for drawing liquid samples and dispensing them into a plurality of test tubes, in particular for drawing biological samples, and dispensing them in a single operation into a plurality of test tubes, filled with air or other gas at atmospheric pressure and containing, if necessary, the additives to preserve or prepare the sample for the requested analyses.

It is known that, usually, the analyses requested for each sample are different both in number and type. It is therefore necessary to use a drawing technique which involves the dispensing of the sample into several test tubes, so that in each of them is ensured the quantity of sample of the purity necessary for a particular analysis.

It is also known that the sample must undergo as little handling as possible to prevent the alteration of its components and, if necessary, it must be mixed as soon as possible to the additives necessary to conserve or prepare it for the requested analyses. This is particularly, but not exclusively, important in the case of a sample of blood drawn out of a patient.

2. Description of the Related Art

U.S. Pat. No. 3,848,581 (Cinqualbre and Cinqualbre) describes three different embodiments of an apparatus consisting of a body providing a longitudinal internal duct connected at one end to a drawing needle and at the other end, through secondary crossducts, to many test tubes, embedded into suitable cavities and left hanging up under said body. In the first and third of said embodiments said test tubes can be filled by shifting them one by one and so opening an outlet to the air contained in them, so that the blood could fill them up in succession to the desired level. In the second embodiment the test tubes are not shifted, the outlet for the air is always open and the test tube to be filled is chosen by shifting a valve member. All the three embodiments are affected by several drawbacks. Lacking any kind of suction means, this apparatus can draw only if a difference of pressure from the drawing element to the atmosphere is present and, in the case of the draws of venous blood, which are normally used, this pressure is very low; this means that the blood flows very slowly and tends to clot, so blocking the flow; to prevent this effect large ducts are required and in particular a large needle, which may be impossible for some patients. The need to manipulate the test tubes or the valve members to open an outlet to the air focuses the operator's attention away from the patient, upon whom it should on the contrary be concentrated, and keeps both of his or her hands employed, while these should be free and used only to look after the patient. It is impossible to programme the precise quantity of sample to be collected into each test tube, being this left to the skill of the operator. The whole operation is unsafe, because the test tubes are not locked to their recesses and, if their fitting is tight, they are difficult to shift and make it difficult to use the apparatus and, if said fitting is loose, the test tubes are likely to come out and spill their contents, both during the draw, because of some error of the operator or some movement of the patient, and especially during their recovery; even worse, during this last operation, the operator must handle the body of the apparatus which is certainly polluted by the sample while one or more of the filled test tubes have already been taken out, so exposing him or her to a high risk of contamination. The apparatus is completely contaminated by the sample and, being too expensive to be disposable, it must be disassembled and sterilized after each single draw.

U.S. Pat. No. 4,649,967 (Gruenstein Eric I. et Al) describes an apparatus designed to transfer simultaneously samples from one or more containers into a plurality of uptake containers singularly airtightly connected to a common vacuum source through a three positions valve; this configuration makes it possible to disconnect the vacuum source and operate on the containers and the ducts connecting them when the valve is kept in a first position, to suck the samples when the valve is kept in a second position and to stop the flow while mantaining the vacuum when the valve is kept in the third position. This apparatus cannot be conceptually used to collect different preprogrammed amounts of sample into the different uptake containers and therefore it is unsuitable for drawing biological samples, expecially blood. Moreover it has some drawbacks: the suction speed cannot be controlled and the force of said suction may produce some foam, with consequent breaking of the cellular membranes, so damaging the sample during the draw; the depression left inside the test tubes after their filling can be a cause of an unwanted ejection of material at the opening of the valve, so making it probable the contamination of the common bore and in consequence the need to clean of the whole apparatus after each draw.

FR-A-1.247.657 (United Kingdom Atomic Energy Authority) relates to an apparatus designed for collecting a sample of a liquid flow representative of its content during a long period, normally many hours; this is obtained by sucking very slowly a small portion of said fluid out of the flow and into a long pipe connected at the other end to a very slowly varying vacuum source through a bottle, into whose cap an input and an output tubes are airtightly inserted, and then taking said pipe out of the fluid stream and emptying it into said bottle slightly increasing the vacuum. After the change of the bottle the whole process can be started again. Many bottles can be filled with samples collected from many liquid flows using the same vacuum source. This apparatus is designed for collecting samples over a long period in a fixed plant: it needs a plurality of drawing elements and a plurality of valves, one of each for each bottle or test tube, a big vacuum apparatus and a big container connected to a slow flowing source of water or other auxiliary liquid and therefore it is very slow at drawing, cumbersome and unsuitable for mobile applications, such as collecting samples for the normal biological analyses.

EP-A-0107579 (Le Material Biomedical) describes a cylindrical container providing a cap which can slide fluid-tightly into it and is connected to a stem; driving manually said stem, such a container can be filled as a syringe, then said stem is broken, transforming it into something similar to a test tube. By connecting to the drawing needle a hose which is split at the other end into many branches, many test tubes, also of different dimensions, can be filled one after the other during the same draw. This system solves the problem of filling many test tubes in a single draw, but it is awkward to handle; it takes a lot of time to complete a draw and needs the whole attention and the use of both hands of the operator to be carried out; furthermore, it is potentially dangerous for the operator who disconnects the test tubes, which are open, from the branches of said hose, both of them being polluted by the sample which can easily spill over.

EP-A-0154002 (Ferring Biotechnik GmbH) describes a programmable apparatus designed for carrying out researches into the biological rhytm, apt to be carried around by a person and to draw samples of blood at stated time intervals, leaving said person free to go around in a normal way. It is a complex, and therefore expensive, apparatus, designed for a very peculiar use, in which the suction means (a pump) act directly on the means connecting the drawing means (needle) and the containers of the samples and which uses, to store them serially in a hose and dispense them to different containers, a multiple-way valve which is subject to contamination and therefore must be disassembled and sterilized every time the set of drawing operations performed on a person is over. Said apparatus is therefore unsuitable for the normal drawing operations, which need high operating speed, low running costs and well defined procedures of use, because it has a low utilization factor, a uselessly high cost, and it compels the operator to handle frequently potentially contaminated components and therefore to undergo a high risk.

Actually, the necessity to carry out draws, especially of blood, in a swift way and without polluting the sucking element, is increasingly becoming such a pressing necessity that it has urged the development of many devices based on the principle of the indirect suction.

It is known that for achieving this goal are widely used test tubes providing an inside programmed depression, which, when inserted on a secondary needle connected through a duct to the drawing needle, can collect into them by suction a desired quantity of blood. All these devices make it necessary either to pierce the vein as many times as there are test tubes to be filled or to leave the needle inserted into the vein for the time being, while the operator inserts successively the secondary needle into the required test tubes, so compelling him or her to use both hands, which should on the contrary be free for taking care of the patient. Moreover said test tubes have several drawbacks: the depression, generated in them when manufactured, decays with time; the suction speed cannot be controlled and the force of said suction may produce some foam, with consequent breaking of the cellular membranes, so damaging the sample during the draw; their cost is high, much higher than the normal test tubes; a residual depression, which can be the cause of an unwanted ejection of material at their opening with potential contamination risk for the operator, is left inside the test tubes after their filling.

Moreover, devices were developed that make it possible to transform the container used to draw the blood into a test tube.

For instance, EP-A-0107578 (Le Material Biomedical) discloses a particular cylindrical container providing a cap which can slide fluid-tightly into it and is inserted in between a drawing needle and a syringe through two couplings also fluidtight; by moving manually the piston of the syringe, a depression is generated upstream of said cap which therefore will slide from the needle end side to the syringe end side, while sucking, in consequence, the blood into said cylindrical container on the other side of the cap, so transforming it into something similar to a test tube. But such a device can only be used to draw a fixed quantity of sample, because the movable element must run through the whole stroke to reach the position in which it surely seals the outlet from which the air was sucked out. Therefore, even if it were modified so as to fill in one stroke several test tubes, this solution would be complex to assemble and disassemble and therefore dangerous to use, and it couldn't anyway provide, as necessary, a collection of predetermined different quantities of sample into each of a plurality of test tubes according to the needs. Also, an immediate mixing with any additives requested could not be provided.

U.S. Pat. No. 4,216,782 (Sarstedt) discloses a similar cylinder providing an inside cap, which slides fluid-tightly, where the sample is collected and can afterwards be used as a test tube, but into which, before the draw, a depression is generated, so performing the draw in a way similar to that previously seen for test tubes with a programmed depression inside. This device has the same drawbacks already seen and one more, that is the need to pierce the vein as many times as there are test tubes to be filled.

EP-A-0150127 (Bilbate Limited) discloses a special syringe which makes it possible to carry out a draw by pushing a piston instead of pulling it out, and therefore using only one hand. According to said patent the blood is collected directly into a test tube sealed by a membrane, into which two needles are inserted, a sucking one connected to said syringe and the other connected to the drawing needle, inserted into a removable component which houses the drawing needle too. Such a device makes it necessary either to carry out as many draws, and therefore to pierce the vein as many times, as there are test tubes to be filled or to dispense later the sample into the requested test tubes, and it is extremely critical to use, because no support is provided for the test tube which can easily slide off the needles during the draw, and in addition is placed necessarily in contact with the patient's arm with no support, in a clearly precarious position. Moreover, after the draw, it is necessary first of all to extract the test tube, leaving to the operator the task of screwing out of the syringe the removable component which has two bare needles exposed, polluted by the sample. This operation is extremely dangerous.

U.S. Pat. No. 5,110,557 (Brown Bradley V. et Al) describes a hand held blood sample collection apparatus providing a special test tube with a special cap, into which the blood is sucked by means of a battery powered vacuum pump; being the core of the invention the actual configuration of said cap and of its connections, it can structurally be used for one test tube only, since said cap is designed for one single test tube. Such an apparatus may be seen as a improved version of a normal syringe, but it sums up some of the drawbacks of the use of a single syringe—the quantity of sample collected is not exactly programmable, the blood must be later manually dispensed to all the necessary test tubes—to some of the drawbacks of the test tubes with an inside programmed depression—the velocity of the inflow cannot be controlled, with all the inherent consequences.

Among all these devices the only ones of widespread use are, in spite of their mentioned drawbacks, those sucking the sample into a test tube within which a depression is produced either at their manufacturing or immediately before the draw, while is still widespread the operation in two phases, consisting of the collection of the sample into a single syringe and its successive distribution into many test tubes, a dangerous operation because it exposes the operator to the risk of infection and the sample to a waiting time and some handlings which might spoil it.

SUMMARY OF THE INVENTION

The aim of the present invention is to overcome the mentioned drawbacks of the known techniques by providing an apparatus which makes it possible to disconnect all the parts potentially polluted by the sample from the other parts, by incorporating these parts in a single unit which may be easily, safely and cheaply disposed of after use, and also makes it possible to draw the sample at the desired speed and dispense a preprogrammed quantity of it directly to each of a plurality of test tubes with the maximum of simplicity, speed and certainty of no contamination, with one single operation which can be carried out as automatically as desired.

A further aim is to provide an apparatus as previously outlined which, for instance for the above mentioned case of drawing blood from a patient, makes it possible for the operator during the whole operation to keep his or her hands free, so permitting to the operator to take only care of the patient, and without either extracting the needle or disconnecting it from the test tubes.

These aims are achieved, in accordance with the present invention, by an apparatus for drawing liquid samples, in particular biological samples, and dispensing them into a plurality of test tubes, which apparatus comprises a single drawing element and a plurality of test tubes filled with air or another gas at atmospheric pressure and kept in a substantially vertical position, containing, if necessary, the additives to preserve or prepare the sample for the requested analyses. The apparatus further comprises first, preferably at least partially flexible connecting means linking continuously during the whole draw the drawing element to each test tube, suction means, and second connecting means linking each test tube to the suction means. Closing means, are provided for sealing the test tubes while allowing the airtight passage of the terminals parts of the first and second connecting means into each test tube. In addition, means are provided for disconnecting the second connecting means and therefore all parts upstream of the connecting means, in the sense of fluid flow, of the apparatus from all downstream parts including the suction means. The upstream parts of the apparatus, comprising the first connecting means and the second connecting means, are merely composed of duct means suitable for freely and directly conveying a fluid flow without any interposition of controlled valve means of flow control means which may require handling during the draw. The downstream parts including the suction means comprise volume control means apt to preprogram the volume of air or gas sucked out of each test tube and therefore the amount of sample dispensed to the test tube, and flow control means apt to control the flow of the sample during the draw.

A method in accordance with the present invention is directed to drawing liquid samples and uses an apparatus as discussed above, particularly suited to drawing potentially contaminated and dangerous samples such as blood, requiring high safety against contamination, short time of operation and constant control by the operator during the whole process. The method comprises three successive phases, namely, a preparation phase, a draw phase and a recovery phase. The preparation phase comprises inserting test tubes into a rack and programming for each of them the quantity of sample to be collected in it, timing the draw if requested, assembling, if necessary, a linking element into a container, coupling the test tubes to the linking element and assembling device, and coupling the device to the box containing the programmed suction means, so completing the apparatus. The draw phase comprises placing the drawing element in the sample collecting position, carrying out the draw, and extracting the drawing element. The recovery phase comprises disassembling the apparatus and the device, extracting and disposing of the linking element, recovering the test tubes one by one, and labeling each of them with the code of identification of the sample or that of the patient. All the programming operations are aimed at obtaining precisely the desired quantity of sample collected into each particular test tube and the desired speed of collection of the sample are carried out before the draw and separately from it, by acting only on those parts of the apparatus downstream of the disconnecting means which are neither flowed through nor contacted by the sample. At every time during the draw, the operator can take over overriding the apparatus, which has been preprogrammed, by acting on manual control means, downstream of the disconnecting means, to regulate the flow of the sample at best for each particular draw and to meet safely any unforeseen situation. All parts of the apparatus upstream of the disconnecting means are disconnected as a whole from the parts downstream of the disconnecting means and the parts polluted by the sample, lodged in the container of the upstream part, are suitably disposed of and discharged after use as a whole. The assembling and programming of the apparatus, the draw and the disposal of the polluted upstream parts and the recovery of the test tubes, are carried out at different moments and therefore can be carried out by different operators.

Due to the fact that means are provided for disconnecting the second connecting means, and therefore all parts upstream of said connecting means, in the sense of fluid flow, of the apparatus from all downstream parts including the suction means and volume control and preprogramming means, said upstream parts being merely composed of duct means without any interposition of valves or flow control means, all parts polluted by the sample can be separated and disposed of safely for the operator and at a low cost, while the relatively costly downstream parts, including the suction means and volume control and preprogramming means, can be repeatedly used for many successive draws without any need to clean or change them, making it possible at the same time a distribution of a preprogrammed quantity of sample into a plurality of test tubes at the flow speed required for that particular sample in that particular case, using a single drawing element and test tubes at atmospheric pressure. In a suitable arrangement for the first and second connecting means for achieving the above results, the first connecting means are composed of a single duct connected, at one end, to the drawing element and split up, at the other end, into a plurality of branches linking the duct to the first end needles. In addition, the second connecting means are composed of a plurality of separate ducts which are extensions of the second end needles linking them to the suction means through the disconnecting means.

Suitably the closing means of the test tubes are pierceable caps of soft elastomer material and the terminal parts of the first and second connecting means are, for each test tube, a pair of first and second end needles apt to pierce through its cap. This solution, as per se known, makes possible an airtight removable connection to the inside volume of each test tube.

Suitably the air suction means are composed of as many sucking devices as the test tubes, each sucking device being apt to be operated so as to suck out of each test tube the volume of air corresponding to the quantity of sample to be collected into it.

Advantageously the air suction means are composed of a single sucking device, selecting means and a control system which makes possible the controlled and programmed suction of the air out of each test tube so as to dispense to each test tube the sample in the predetermined quantity and sequence.

Suitably the single duct and the branches of the first connecting means and the ducts of the second connecting means are at least partially located and incorporated into a linking element, preferably made of plastics and disposable after use, into which the pairs of end needles are fluid-tightly inserted and equipped with airtight couplings to the suction means. This solution makes it easier to assemble the apparatus and it makes possible a safe disposal of the parts through which the sample flowed.

Preferably the end needles of the second connecting means end up into the test tube at a higher level than that of the corresponding end needles of the first connecting means. This solution makes it possible to prevent the air sucking needle from sucking part of the sample too.

Due to the fact that the apparatus, is assembled and programmed before carrying out the draw and the test tubes are taken out and labelled after this operation, it is possible to perform independently the preparation of the apparatus, the draw and the handlings of the test tubes; these three operations can therefore be carried out also by different operators in different moments. This procedure in some cases, for instance for the already mentioned case of the draw of blood, makes it possible to shorten the time devoted to each patient and in consequence the waiting times, so increasing the efficiency of the service.

It is possible to collect an exact quantity of sample into each test tube and therefore to draw the least necessary total quantity, which is very useful in particular for the draw of blood out of a patient.

The inflow speed is controlled, therefore it is possible to adjust it to the particular circumstances of each draw.

The capability of autonomous running of the equipment, which can be started by an operator or by a control system, makes it unnecessary for the operator to use both hands to handle the equipment during the whole operation, so leaving his or her hands free just for taking care of the patient.

The combination of the previously mentioned elements makes it possible to keep unaltered in the time the position and the conditions of the draw also for draws made at different times and it is useful when comparative analyses of samples collected at time intervals are to be made, because it makes possible to obtain comparable results and simplify the automation of the methods.

BRIEF DESCRIPTION OF THE DRAWINGS

This invention will be better understood from an examination of the description and of the figures relating to some exemplifying and not limiting embodiments of this invention.

In particular

FIG. 10 shows the scheme of a further embodiment of an apparatus with six test tubes according to the present invention.

DESCRIPTION OF THE PREFERRED EMBODIMENTS

Equal elements of the same figure are labelled with equal numbers, followed by a different subscript which in the description is omitted, where not necessary, for the sake of simplicity.

As will be apparent from the present description to those expert in the several fields which this invention can be applied to, an apparatus according to this invention can be embodied in many different ways, at different levels of technology and automation, using on the whole known techniques.

Figure 1:
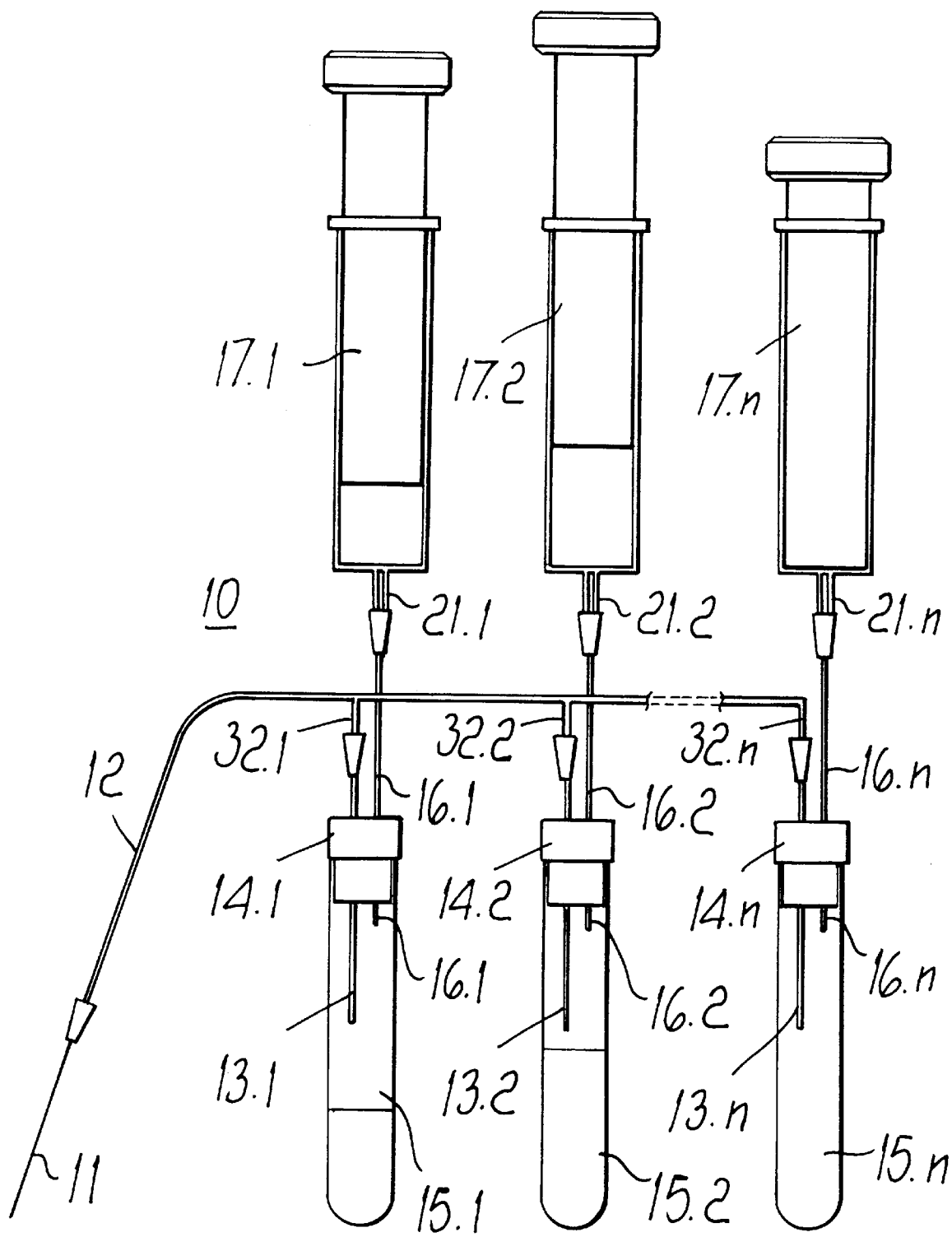
FIG. 1 shows the basic scheme of the simplest embodiment of an apparatus according to the present invention.

As a non limiting instance FIG. 1 shows the simplest conceivable way to embody the apparatus 10 according to this invention. A drawing element 11 is connected through first connecting means consisting of a duct 12, n branches 32 and n end needles 13 inserted into closing means consisting of n caps 14, pierceable and airtight, made of rubber or other soft elastomer material, of n test tubes 15 filled with air or other gas at atmospheric pressure, kept in a vertical or quasi-vertical position. Into the same caps are also inserted needle-like extensions of second connecting means 16. Disconnecting means 21 disconnect said second connecting means 16 and therefore also all the other parts 11, 12, 32, 13 of the apparatus 10 upstream of them, in the sense of the flow, from all downstream parts including the suction means, said suction means consisting of n syringes 17. By sucking successively into each syringe a suitable volume of air, it is possible to collect into the corresponding test tube the desired quantity of sample. To prevent a possible suction of the sample out of the test tube, it is useful that the end needle 16, connected to the duct sucking the gas, be much shorter than the end needle 13, which carries the sample into the test tube, so that for no reason said end needle 16 be allowed to approach the liquid surface and dip into it.

Figure 2:
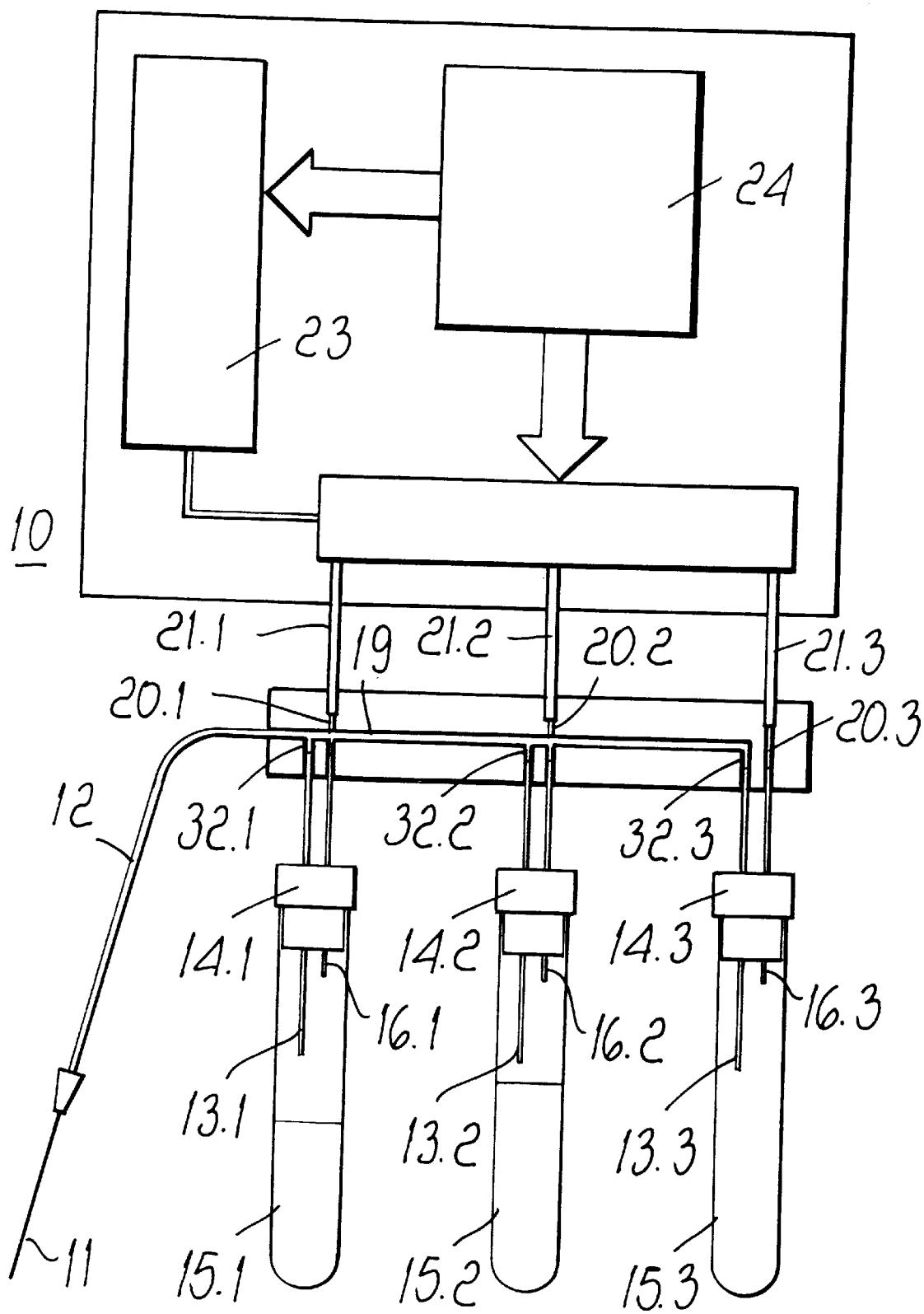
FIG. 2 shows the functional scheme of an apparatus according to the present invention using a single suction means.

The suction means may be embodied either by a plurality of equal separate elements assembled together, as seen in the previous case, or by a single device, as shown in FIG. 2.

FIG. 2 shows the overall scheme, referred to such an apparatus for three test tubes. This apparatus consists of a control system 24 controlling a single device 23 sucking at controlled speed and a selecting means 22. The control system connects orderly selection means 22, connected to the sucking device 23, to the test tubes 15.1,15.2, . . . , 15.n through the disconnecting means 21.1,21.2, . . . , 21.n and the second connecting means 16.1,16.2, . . . , 16.n, so sucking from each of them, under control, a given volume of air.

Figure 3:
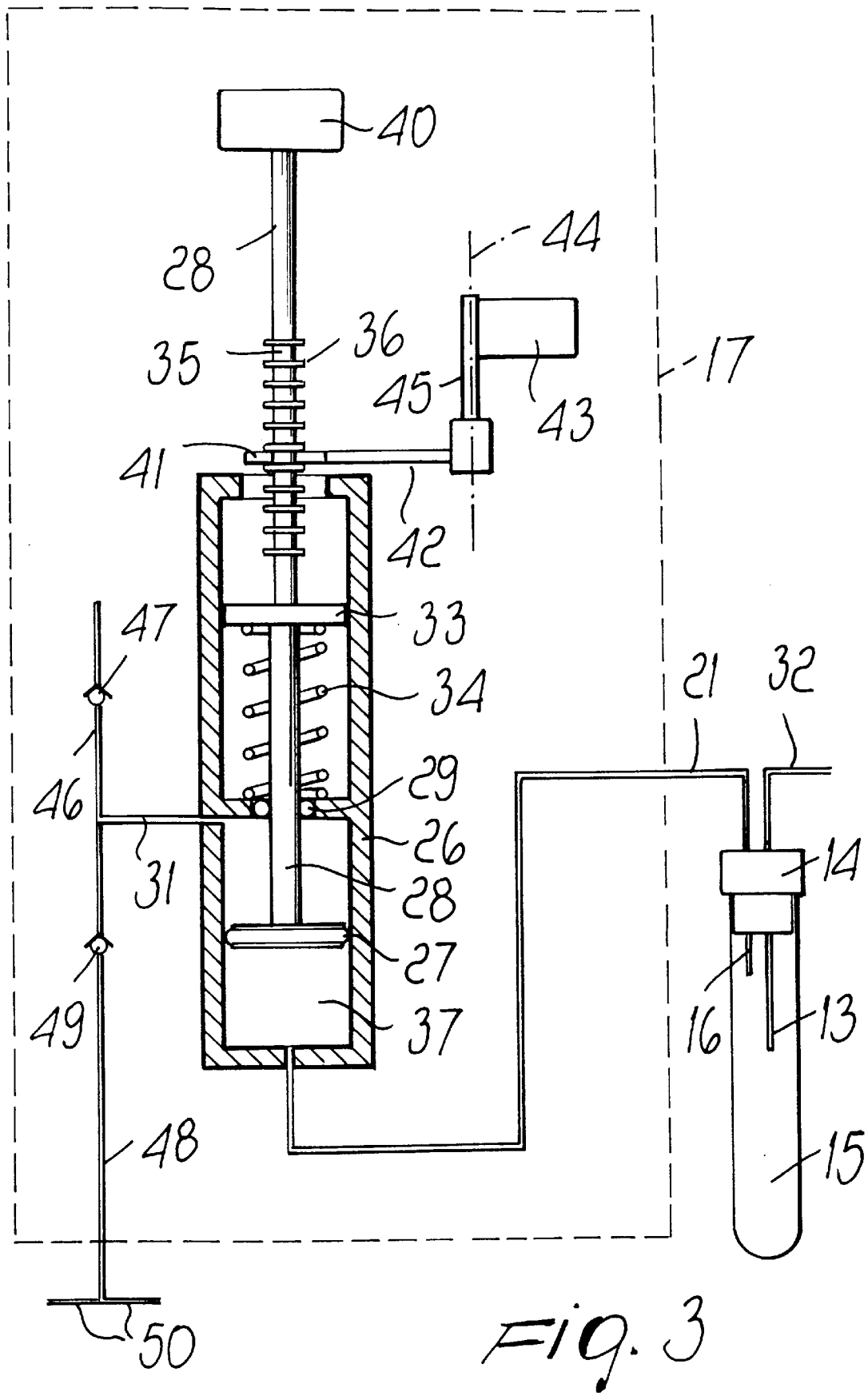
FIG. 3 shows the plan of an embodiment of a device sucking from one test tube according to the invention.

FIG. 3 shows a simple way to embody an element 17 for sucking under control the air out of a test tube. It shows a cylinder 26 into which slides an airtight piston 27 whose stem 28 slides, also airtightly, in a sliding gasket 29, so that the air can flow into and out of the upper stem side chamber 30 only through a duct 31. Said stem 28 on its external upper part is provided with a flange 33, apt to compress a spring 34 when the stem is pressed toward the lower part of said figure, and an extention 35 of said stem beyond this flange is provided with many retainers or teeth 36 spaced along it at equal distances so that the piston, when moving said stem from one retainer to the next one, will suck into or expel out of the lower sucking chamber 37 a well predetermined volume of air, for instance of one cubic centimetre. Said stem 28 ends up with a knob 40 apt to move it manually and may be locked into a certain number of predetermined positions through a fork 41, or another equivalent ratchet gear, engaging with the groove between two retainers 36; said fork 41 is connected to a rod 42 integral to a shaft 45 which, manually moved through a trigger 43, rotates around an axis 44 parallel to that of the piston 28. For sucking a given volume of air out of a test tube 15 through the disconnecting means 21 and the end needle of the second connecting means 16 airtightly inserted into its cap 14, the piston 27 is moved, pushing the knob 40, by a stroke corresponding to the volume which is to be sucked, measured by the number of retainers which the locking fork 41 leaves behind, then the stem 28 is locked by said fork through the trigger 43; during this operation the spring 34 is compressed by the flange 33. This operation is preferably carried out before connecting the test tube 15 to the sucking device 17. During this operation the stem side upper chamber 30 becomes filled with air through the ducts 31 and 46 and the unidirectional valve 47. For sucking the sample into the test tube 15 through the end needle 13 connected to the input duct 32, the operator does nothing but unlock the stem 28 by pushing the trigger 43; then the spring 34 will push upwards the flange 33 and the stem 28, so that the piston 27 will suck the air into the lower sucking chamber 37 and out of the test tube 15 and expel the air out of the upper stem side chamber 30 through the duct 31, the unidirectional valve 49 and the ducts 48 and 50, until said piston 28, pushed by the spring 34, has reached its rest position, that is the upper limit of its stroke, having consequently sucked the desired quantity into the test tube 15.

Figure 4:
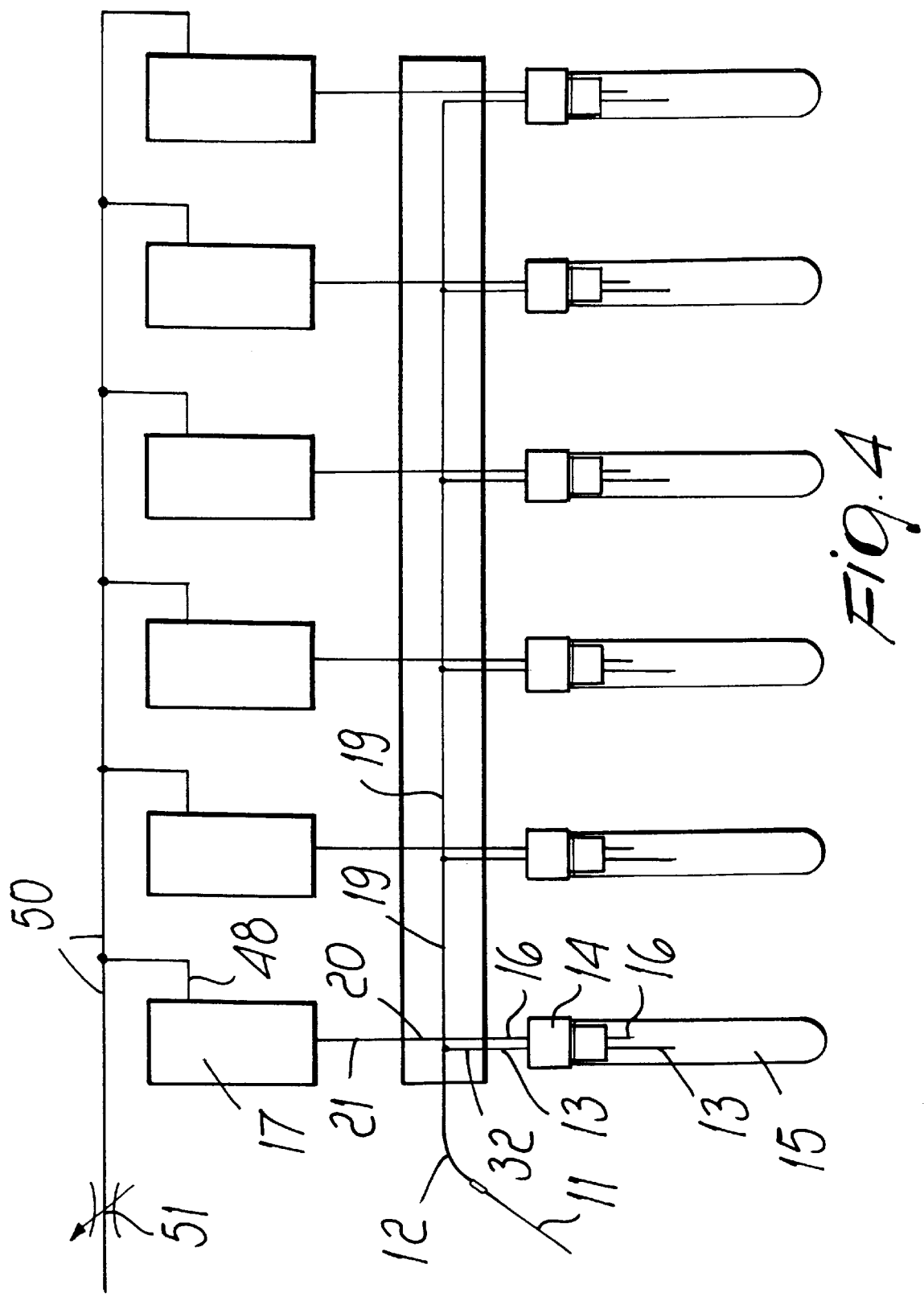
FIG. 4 shows the scheme of an apparatus for six test tubes using said sucking device.

FIG. 4 shows the scheme of an apparatus with six test tubes using the sucking devices of FIG. 3. In it the six test tubes are connected to as many sucking devices 17 and to the drawing element 11. The ducts 48 through which the air flows from the stem side chambers 30 of the six sucking devices 17 end up in a common manifold 50 connected to the atmosphere through a manually controlled flow control valve 51, which makes it possible to control, from zero to a maximum stated value, the outflow from the upper stem side chambers 30 and in consequence the translation speed of the piston 28 and the inflow speed of the fluid into the test tube 15.

It is important that all the upstream part, polluted by the sample, can be easily, safely and cheaply disposed of. This can be obtained in a preferred embodiment of the invention by using a linking element 18, preferably made of plastics and of different dimentions according to the number of test tubes 15 involved, which can be inserted on said test tubes in an univocally determined position, as will be better specified later with reference to the FIGS. from 5 to 9. Said linking element 18 provides at one end a hose 12, ending up into the drawing element 11, and a duct 19 inside, as an extension of hose 12, comprising branches 32, which connect the hose 12 to the longer end needle of the first connecting means 13 of every pair of needles. Moreover it provides as many separate through ducts 20 as the test tubes upon which it has to be inserted. One end of the duct 20 is connected to the shorter end needle of the second connecting means 16 of the pair and, at the other end upstream half-coupling means 20A are provided, mating airtightly with downstream half-coupling means 21B of the corresponding disconnecting means 21 connecting it to the suction means 17.

The linking element 18 can be made either in one piece or by assembling modular components, either one for each test tube or one for two or more of them.

Figure 5:
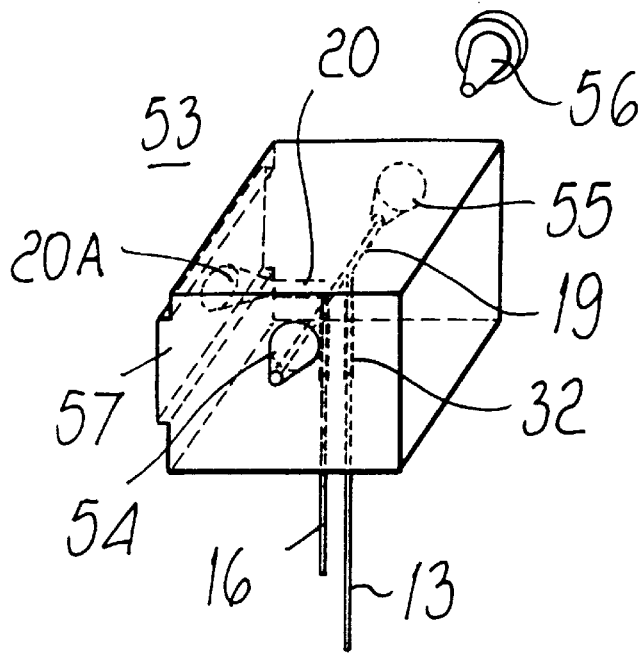
FIG. 5 shows the axonometric outline of a modular element linking the suction means, the drawing element and one test tube.

FIG. 5 shows an instance of modular assemblable linking component 53, apt to be inserted into a single test tube and to mate with other equal ones. It consists of a parallelepiped, normally made of plastics, providing on its lower face the two end needles 13 and 16 of different length. The longer end needle 13, through which the sample flows, is connected, through the vertical duct 32, to an horizontal through duct 19, which connects two half coupling means 54 and 55, placed on two opposite faces of said parallelepiped, and apt to be fluid-tightly inserted into corresponding half coupling means 55 and 54 of other equal components 53; into the half coupling means 54 can also be fluid-tightly inserted the hose 12 connected at its other end to the drawing element 11. The shorter end needle 16 is connected, through an elbowed duct 20, to half coupling means 20A, placed on one of the lateral faces of said parallelepiped and apt to mate with a corresponding half coupling means 21B of the disconnecting means 21 connected to the suction means 17. Said face provides a raised strip 57 which makes possible a correct positioning of the linking element 18, as made more evident in FIGS. 7 and 8. Of course the same result can be obtained in different ways too, as it will be apparent to those expert in the field. These components are connected one another, one for each test tube which has to be filled, so as to provide a continous duct 19 through which the fluid sample can flow. To make possible this draw, the duct must be open only on the drawing element side; this can be obtained in many ways, in particular with a cap 56 fluid-tightly forced into the half coupling means 55 of the last component 53 of the chain.

The linking element 18, be it of a single piece or formed as a chain of modular components 53, must always be positioned on the test tubes which are to be filled, so that the end needles 13 and 16 are inserted into them.

Figure 6:
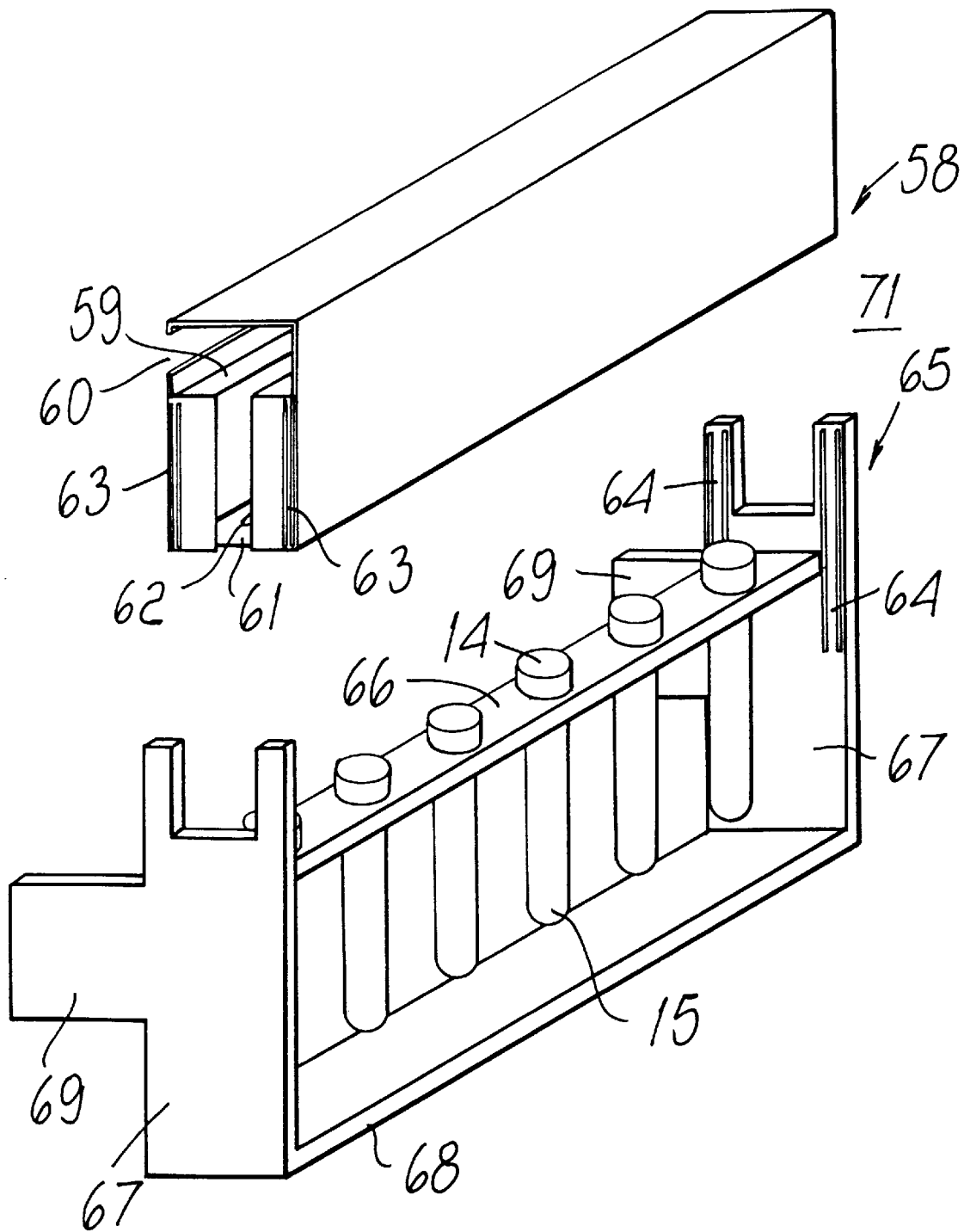
FIG. 6 shows the axonometric outline of a rack lodging the test tubes and a container lodging the linking element.

FIG. 6 shows an exploded view of a device 71, consisting of two superposed parts 58 and 65, apt to be joined easily. The upper part is formed by a container 58 comprising an upper guide 59, into which the linking element 18 (not shown in the figure) can be longitudinally inserted, this guide being open downwards so that the pairs of end needles can slide into it, and a longitudinal slit 60, into which the raised strip 57 of the modular components 53 (FIG. 5) can slide, if the linking element is formed by such components. Longitudinally the linking element 18 is placed and removably locked in the requested position through devices made with known techniques and therefore not shown in the figure. The lower side of the container 58 is closed by a flat horizontal element 61 apt to slide upwards parallel to itself and biased downwards by a set of springs made with known techniques and therefore not shown in the figures; this element 61 provides slits 62 of dimensions and position such that the pairs of end needles can pass through them when it is pushed upwards. The right and left sides of this container are connected by cross links placed below the upwards movable element 61, which are not shown in the figure for clarity. The lower part 65 is a rack formed by a bottom plate 68, two vertical end shoulders 67 and an horizontal crosspiece 66 which provides as many lodgings placed at equal distances as the test tubes which can be filled, six in this example, into each of which one test tube can be inserted so that only its cap will emerge from said crosspiece. For simplicity sake all the test tubes, and therefore their lodgings, are shown to be of equal size in the figures, but in the actual use it may be necessary to use test tubes of different dimensions; this is not a problem, since it is well known that suitable adapters can be used to fit different test tubes into equal lodgings.

After its assembling, the upper part 58 of the device 71 is vertically inserted into the lower one 65, through two pairs of guides 63 sliding along two pairs of corresponding guides 64 placed on the inward sides of the shoulders 67 of the lower part 65.

Figure 7:
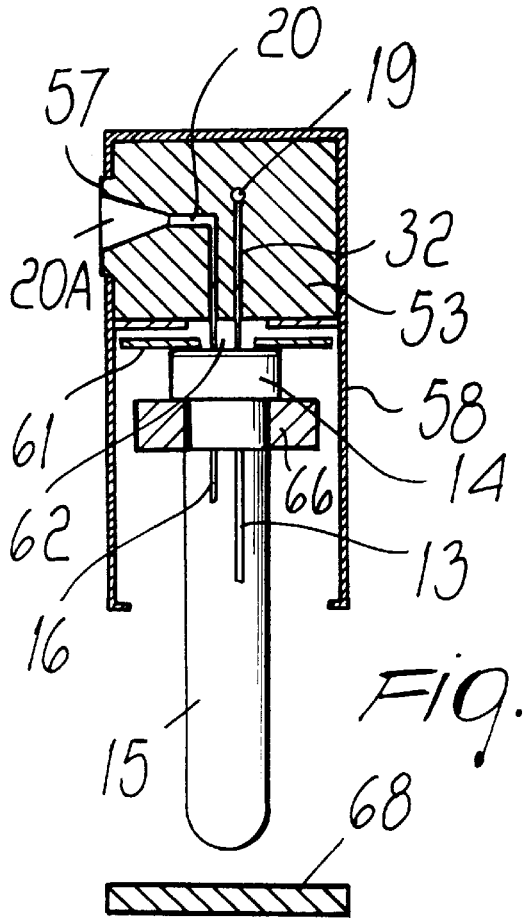
FIG. 7 shows the I—I cross section of a linking element and a test tube assembled and inserted one into the other.

While carrying out this operation the flat horizontal element 61 of the upper part 58 is pushed upwards, the pairs of end needles 13 and 16 will pass through the slits 62 and pierce the caps 14 of the test tubes 15. To make this more evident the FIG. 7 shows the cutaway cross section of said device 71 in a plane containing the axis of a test tube and parallel to the shoulders 67 of the lower part 65, after its assembly.

Figure 8:
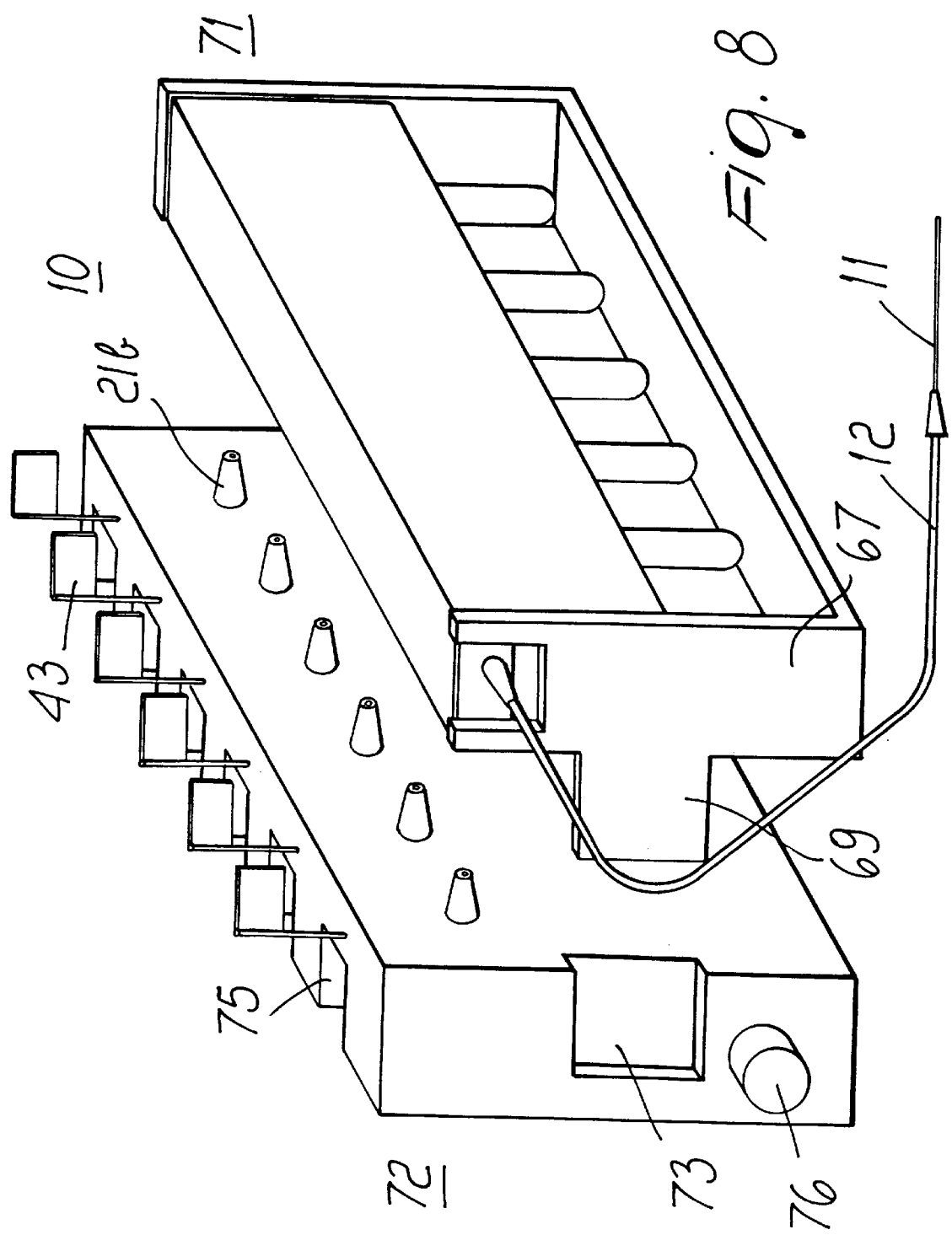
FIG. 8 shows the axonometric outline of an apparatus similar to that of FIG. 4, apt to draw a sample of blood, during the preparation phase immediately preceding said draw.

After its assembly, the device 71 is laterally coupled to a box 72 (FIG. 8) containing the suction means 17, not shown in FIG. 8 which shows only the half coupling means 21B of the disconnecting means 21 mating the half coupling means 20A connected to the end needles of the second connecting means 16. The assembly of device 71 and of box 72 is obtained through two guides 69 jutting out of the shoulders 67 of the lower part of device 71 and corresponding guides 73 connected to said box 72, which can slide one into the other, so joining them and locking said assembly through two hooks, which can be manually unlocked. These hooks can be made with known techniques and therefore are not shown in the figure. During this operation, the half coupling means 21B of the disconnecting means 21 placed on the inner lateral side of the box 72 mate airtightly with the half coupling means 20A of the linking element 18, or of its components 53. In FIG. 8 are also shown grooves 75 into which the knobs 40 will slide when the springs 34 are compressed (FIG. 3), as well as triggers 43 (more visible in FIG. 3) which lock and unlock said springs and a knob 76 controlling the valve 51 which controls the outflow of the air and consequently the inflow of the sample.

Figure 9:
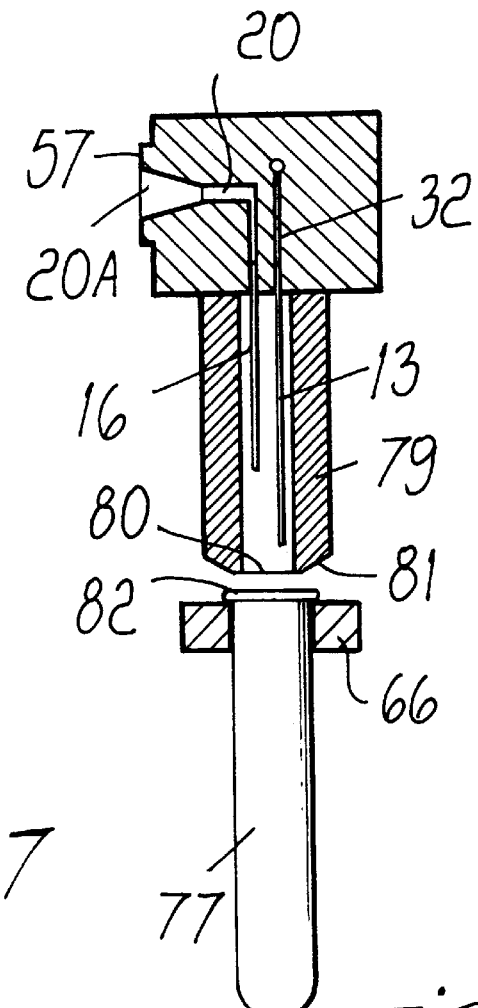
FIG. 9 shows a simplified plan of the I—I cross section when open test tubes are used.

When possible, it might be useful to use open test tubes, because of their much lower cost; in this case the apparatus previously described can also be used if the linking element 18 is made so as to provide a closing part, of which an example is shown in FIG. 9, apt to guarantee the airtight sealing of the test tubes during the whole drawing operation. Said FIG. 9 shows a cutaway cross section in a vertical plane corresponding to that of FIG. 7 of an open test tube 77 and a linking component 78 before inserting the container 58 of the device 71 on its lower part 65 (FIG. 6). For the sake of simplicity, in FIG. 9 all that is not essential to explain the concept is omitted. The linking component consists of an upper body and a pair of end needles quite similar to those of the component 58, but provides also a tubular appendix 79, connected to its lower side and coaxial to the pair of end needles 13 and 16, made of soft very compressible material apt to adhere to the upper edge 82 of the test tube 77 with a truncated cone surface 81 and sealed in its lower part by a membrane 80 which can be pierced by said end needles. When the container 58 is inserted into the lower part 65 of the device 71, said surface 81 is compressed against the edge 82 of the test tube by the compression of the tubular appendix 79, so making their coupling airtight, and the end needles 13 and 16 will pierce the membrane 80 and enter into the test tube 77, making so possible its filling. Of course said linking components 78 can only be used if the slits 62 of the lower flat element 61 of the container 58 are sized so as to allow the passage and compression of the tubular appendix 79.

As previously said and shown in FIG. 2, the suction means 17 can also be embodied in a single device 23, the suction being switched from one test tube to the next one through a selecting means; as it is known to those skilled in the field, there are many ways for embodying such a device, at different technological levels, ranging from clockwork spring driven units to electronic control systems.

FIG. 10 shows the scheme of an apparatus 10 with six test tubes in which an electronic control system 24 controls a sucking device 23 composed of a cylinder 83 driven by a motor 86, for instance a step motor, through a lead screw drive formed by a screw 84 coupled to a nut screw 85. Said sucking device 23 is successively connected to the test tubes 15 and, at the end of the operation, to the atmosphere through the outlet 87, for driving back the piston 88 to the starting point, through the selecting means 22. These may be for instance electrovalves, also controlled by the control system 24. Said control system is programmed using the selectors 89 and started, and if necessary stopped, using a pushbotton 90; the sucking speed can be controlled by varying the speed of the motor 86 through a knob 91.

Figure 11:
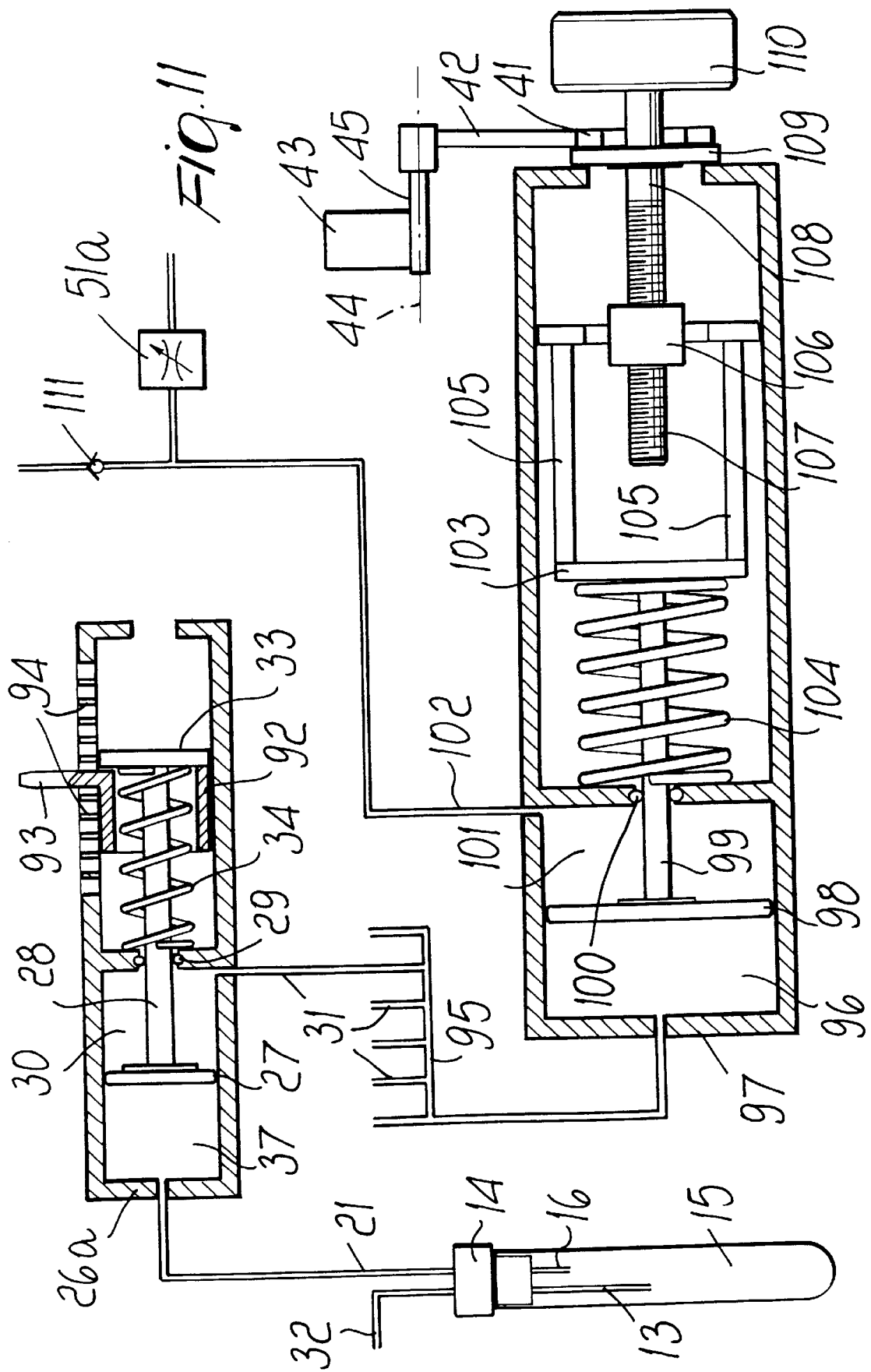
FIG. 11 shows the plan of yet a further embodiment.

FIG. 11 shows another embodiment of the apparatus 10. It shows the longitudinal cross section of a primary cylinder 26a, partially equal to the cylinder 26 of FIG. 3, into which slides fluid-tightly a piston 27, whose stem 28 slides, also fluid-tightly, through a sliding gasket 29, so as to make it sure that the fluid filling the stem side chamber 30 can flow into and out of said chamber only through the duct 31. Said stem 28 provides at the other end a flange 33 apt to compress a spring 34. Coaxial to and outside of said spring 34, there is a annular element 92 so sized as to act as a retainer of the flange 33, which can be axially displaced and locked through a set of grooves 94 and a lever 93; said grooves 94 are so spaced that, when moving said stem from one groove to the next one, the volume of the sucking chamber 37 will change by the minimum quantity which is required to draw, for instance one cubic centimetre. The duct 31 ends up into a common manifold 95 together with other similar ducts 31 of the other cylinders 26a, six in the figure, only one of which is shown for the sake of simplicity; the common manifold 95 connects the ducts 31 to the sucking chamber 96 of a secondary cylinder 97, so that the stem side chambers 30, the ducts 31, the common manifold 95 and the sucking chamber 96 of the secondary cylinder 97 will form on the whole a closed volume, filled with a primary fluid, preferably a liquid. Into said secondary cylinder 97 slides fluid-tightly a piston 98, whose stem 99 slides, also fluid-tightly, through a sliding gasket 100, so that the fluid filling the stemside chamber 101, in this instance air, can flow into and out of it only through the duct 102; the outflow from the stem side chamber 101 is controlled through a flow control valve 51a, quite similar to the valve shown in FIG. 4, while its fast filling is made possible by the unidirectional valve 111. The stem 99 provides at the other end a flange 103, apt to compress a spring 104, and is integral to a structure 105 providing a nut screw 106 coupled to a screw 107. Said screw 107 ends with a stem 108 provided with a flange 109, apt to be stopped against the terminal part of the body of the cylinder 97, and can be rotated through a knob 110. Said flange 109 is locked against said body of the cylinder through a locking device quite similar to that shown in FIG. 3; in it a fork 41 is mounted on a rod 42 integral to a shaft 45 which, driven by a trigger 43, rotates round an axis 44 parallel to the axis of the cylinder 97; also in this case, for the sake of simplicity, the structure supporting the shaft 45 and linking it to the cylinder 97 is not shown in the figure, since it is made with known techniques.

To perform a draw, each annular element 92 is shifted to the left by a number of grooves 94 corresponding to the volume which is to be collected into the respective test tube 15, then the knob 110 is rotated. As a result the piston 98, by pushing the fluid out of the sucking chamber 96 into the stem side chambers 30 through the common manifold 95 and the ducts 31, will shift the pistons 27 untill the flanges 33 are stopped by the annular elements 92; to avoid a possible breakdown of the apparatus, the knob 110 must be equipped with a torque limiting device, not shown in the figure since it is made with known techniques. The test tubes 15 are placed into the apparatus and the drawing element (not shown in the figure) is inserted. When the trigger 43 is unhooked, the fork 41 unlocks the flange 109 and consequently the spring 104. This spring shifts the piston 98 which sucks the fluid out of the stem side chambers 30. This causes the pistons 27 of the primary cylinders 26a to go back to their rest positions, consequently collecting into the corresponding test tubes 15 the programmed quantity of sample; the springs 34 cooperate with said spring 104 to make sure that the pistons 27 go always back to their rest positions to ensure the precision of each draw. In such an apparatus the sucking speed of the sample is controlled only by the speed of the stem 99, with no connection to the actual flow into each test tube during the draw. As it is apparent to those skilled in the field, the speed of the stem 99 can be controlled in many different ways; in the example shown in the figure, said speed is controlled by controlling the outflow of the air filling the stem side chamber 101 through a flow control valve 51a; mounted in parallel to said valve, there is an unidirectional valve 111, apt to make it possible the fast filling of the stem side chamber 101.

The operating sequence, particularly suited to drawing potentially contaminated and dangerous samples, such as blood, requiring high safety against contamination, short time of operation and constant control by the operator during the whole process, is generally carried out as detailed below, with reference to claim 17; of course, according to the actual use of the apparatus, some of the listed operations can be unnecessary and therefore omitted.

The operating sequence comprises three successive phases as follows, which can be carried out in different moments and therefore by different operators at different levels of skill; this can be very important because it simplifies the whole drawing operation, by shortening the time necessary for each patient and therefore raising the productivity and reducing the cost of the analyses.

A preparation phase, which requires a low level of skill and can be carried out directly at the reception, comprises:
  inserting the test tubes 15 into a rack 65 and programming for each of them the quantity of sample to be collected in it;
  if requested, timing the draw;
  assembling, if necessary, a linking element 18 into a container 58, coupling the test tubes 15 to said linking element and assembling the device 71;
  coupling the device 71 to the box 72 containing the programmed suction means 17, so completing the apparatus 10.

All these assembling and programming operations, aimed at obtaining precisely the desired amount of sample collected into each particular test tube 15 and the desired speed of collection of the sample, are carried out before the draw and separately from it, by acting only on those parts 72 of the apparatus 10 downstream of the disconnecting means 21 which are neither flown nor contacted by the sample and therefore can be reused as many times as necessary without cleaning.

A draw phase, which must be carried out by a skilled operator, comprises:
  placing the drawing element 11 in the sample collecting position;
  carrying out the draw; at every time during the draw the operator can take over, overriding the apparatus, by acting on manual control means 51, 51a, 91 downstream of said disconnecting means, to regulate the flow of the sample at best for each particular draw and to meet safely any unforeseen situation;
  extracting the drawing element.

A recovery phase, which can be carried out when beginning the preparation of the samples, comprises:
  disassembling the apparatus 10 and the device 71; all the parts of the apparatus 10 upstream of the disconnecting means 21 are disconnected as a whole from the parts 72 downstream of said disconnecting means;
  extracting and disposing of the linking element 18; the parts polluted by the sample 11,12,18, lodged in the container 58 of said upstream part 71, are suitably discharged and disposed of after use as a whole;
  recovering one by one the test tubes (15), labelling each of them with the code of identification of the sample or that of the patient.

Using such a procedure with an apparatus implemented according to this invention makes it possible the easy disposal of the complete polluted part as a whole, so obtaining the safest possible handling of such a dangerous elements in the cheapest way.

Sometimes the draw can be carried out through an automatic system, using every time a different method; for instance permanent drawing ducts may be used, or samples may have to be collected into different test tubes at stated time intervals.

Even though this invention is described as relating to liquid samples, it is clear that it can be also used for non liquid biological samples, for instance for the multiple biopsy, only by suitably proportioning the connecting and suction means.

In summary, an apparatus is formed by assembling a drawing element, a plurality of test tubes with airtight pierceable caps and a sucking system, suitably connected through ducts which are at least partially embodied in a disposable linking element, so that while preprogrammed volumes of air are sucked out of said test tubes, programmed quantities of sample are collected into each of them. Some different construction patterns at different technological level and an embodiment of said apparatus are outlined. A method for using it is described.

From the above description it will be apparent to those skilled in the several fields in which this invention can be used that it can be embodied also in ways different from those outlined. This invention is therefore limited only as defined in the following claims.

I claim:

1. Apparatus for drawing liquid samples, in particular biological samples, and dispensing them into a plurality of test tubes, comprising:
  a single drawing element;
  a plurality of test tubes filled with air or another gas at atmospheric pressure and kept in a substantially vertical position, containing, if necessary, the additives to preserve or prepare the sample for the requested analyses;
  first connecting means, preferably flexible at least partially, linking continuously during the whole draw the drawing element to each test tube;

suction means;

second connecting means linking each test tube to the suction means;

closing means of the test tubes, sealing said test tubes while allowing the access to each test tube, of the terminal parts of the first and second connecting means;

wherein:

means are provided for disconnecting the second connecting means, and therefore all parts upstream of said connecting means, in the sense of fluid flow, of the apparatus from all downstream parts including the suction means;

said upstream parts of the apparatus, comprising the first connecting means and the second connecting means are merely composed of duct means suitable for freely and directly conveying a fluid flow without any interposition of controlled valve means or flow control means which may require handling during the draw;

said downstream parts including the suction means comprise volume control means apt to preprogramme the volume of air or gas sucked out of each test tube and therefore the amount of sample dispensed to said test tube, and flow control means apt to control the flow of the sample during the draw.

2. Apparatus according to claim 1 wherein the closing means of the test tubes are pierceable caps of soft elastomer material and the terminal parts of the first and second connecting means are, for each test tube, a pair of first and second end needles apt to pierce through its cap.

3. Apparatus according to claim 2 wherein the first connecting means are composed of a single duct connected, at one end, to the drawing element and split up, at the other end, into a plurality of branches linking said duct to the first end needles and the second connecting means are composed of a plurality of separate ducts which are extensions of the second end needles linking them to the suction means through the disconnecting means.

4. Apparatus according to claim 1 wherein the suction means consist of as many sucking devices as the test tubes each provided with independent programmable control means of the sucked volume.

5. Apparatus according to claim 1 wherein the suction means are composed of a single sucking device, selecting means and a control system.

6. Apparatus according to claim 2 wherein at least a section of the single duct and the branches of said first connecting means and a section of said second connecting means, all of them pertaining to the upstream part of the apparatus, are located and incorporated into a linking element, preferably made of plastics, disposable after use, into which the pairs of first and second end needles are fluid-tightly inserted, said linking element being provided with upstream half-coupling means apt to be airtight coupled to downstream half-coupling means of the disconnecting means.

7. Apparatus according to claim 2 wherein the end needles which are the terminal parts of the second connecting means end up into each single test tube at a higher level than that of the corresponding needles which are the terminal parts of the first connecting means.

8. Apparatus according to claim 2 wherein the suction means are a plurality of equal elements, one for each test tube, arranged side by side, each composed of a cylinder into which slides an airtight piston, whose stem slides also airtightly through a sliding gasket, dividing said cylinder into a sucking chamber connected through said disconnecting means to the second connecting means and a stem side chamber which can be filled with air through an unidirectional valve and an input duct and emptied through an unidirectional valve and an output duct.

9. Apparatus according to claim 8 wherein the terminal part of the output ducts of all corresponding stem side chambers of the cylinders is formed by one single duct connected to the atmosphere through a flow control valve manually controlled by the operator.

10. Apparatus according to claim 8 wherein said stem is moved by an elastic element which is preloaded through a knob, said stem having on its external part a set of retainers spaced along it at equal distances so that, when moving said stem from one retainer to the next one, the volume of the sucking chamber will change by the minimum quantity which can be sucked into the test tube, being possible to lock said stem by means of a ratchet gear which can also be manually locked and unlocked.

11. Apparatus according to claim 6 in which the linking element, preferably made of plastics, can be made at least partially of a plurality of modular components, each provided with a branch and a section of the single duct of the first connecting means through which the sample flows and an output duct necessary to suck the gas out of one test tube and the corresponding end needles and also provided with half coupling means for connecting said modular components so as to form a continuous fluidtight duct from the drawing element to the branch and half coupling means for connecting the linking element to the disconnecting means.

12. Apparatus according to claims 6 and 11, wherein the test tubes are open and both the linking element and the plurality of modular components are additionally provided with integral test tube closing means consisting of a tubular appendix, coaxially lodging two end needles, said appendix being made of soft and very compressible elastomer material and provided with a lower truncated cone surface, so that it can mate airtightly with the upper edge of the corresponding open test tube, and a membrane which can be pierced by said needles.

13. Apparatus according to claim 12 wherein the connection of the test tubes and the linking element, either as a single piece or as an assembly of adjoining modular components, is obtained by means of a device composed of two parts, which can be inserted one into the other, whose upper part is formed by a container into which said linking element can be placed with its needles pointing downwards and the lower one is formed by a holding rack into which said test tubes can be inserted and kept in a vertical position so that, while inserting the upper part into the lower one, the needles of said linking element are inserted into the test tubes below.

14. Apparatus according to claim 13, wherein the device holding the test tubes and the linking element with the needles inserted into said test tubes, is assembled laterally through two suitable guides to a box containing the suction means, so that each half-coupling of the disconnecting means will mate airtightly with a corresponding half-coupling of the linking element.

15. Apparatus according to claim 5 in which the sucking device is composed of a cylinder controlled by a motor through a lead screw drive, the selecting means consisting of a set of electrovalves, and the control system is formed by an electronic programmable circuit.

16. Apparatus according to claim 1, wherein the suction and flow control means comprise as many primary cylinders as the test tubes and a secondary cylinder, each primary cylinder being equipped with a fluid-tight piston provided with a stem sliding also fluid-tightly through a sliding gasket, said piston dividing the primary cylinder into a sucking chamber connected to a test tube and a stem side chamber, auxiliary pulling means of the stem of the primary piston and means apt to limit in a preprogrammable way the stroke of said piston being provided, said stem side chamber being connected through a duct to a common manifold connected at the other end to a sucking chamber of the secondary cylinder equipped with a fluid-tight piston, provided with a stem sliding through a fluid-tight sliding gasket, dividing said secondary cylinder into said sucking chamber and a stem side chamber filled with a secondary fluid, where the stem side chambers of the primary cylinders, the sucking chamber of the secondary cylinder and the connecting ducts form on the whole a closed volume filled with a primary fluid preferably liquid, where driving means of the piston of the secondary cylinder, means apt to limit at will the stroke of the piston of the secondary cylinder and means to control its translation speed, preferably formed by a manually controlled flow control valve, apt to control the outflow speed of the secondary fluid from the stem side chamber of the secondary cylinder are provided.

17. Method for drawing liquid samples, using an apparatus according to claim 1, particularly suited to drawing potentially contaminated and dangerous samples, such as blood, requiring high safety against contamination, short time of operation and constant control by the operator during the whole process, comprising three successive phases as follows:

a preparation phase, which comprises:
   inserting test tubes into a rack and programming for each of them the quantity of sample to be collected in it;
   if requested, timing the draw;
   assembling, if necessary, a linking element into a container, coupling the test tubes to said linking element and assembling the device;
   coupling said device to the box containing the programmed suction means, so completing the apparatus;

a draw phase, which comprises:
   placing the drawing element in the sample collecting position;
   carrying out the draw;
   extracting said drawing element;

a recovery phase, which comprises:
   disassembling the apparatus and the device;
   extracting and disposing of the linking element;
   recovering one by one the test tubes, labelling each of them with the code of identification of the sample or that of the patient and wherein:
   all the programming operations aimed at obtaining precisely the desired quantity of sample collected into each particular test tube and the desired speed of collection of the sample are carried out before the draw and separately from it, by acting only on those parts of the apparatus downstream of the disconnecting means which are neither flawed through nor contacted by the sample;
   at every time during the draw the operator can take over overriding the apparatus, which has been preprogrammed, by acting on manual control means, downstream of said disconnecting means, to regulate the flow of the sample at best for each particular draw and to meet safely any unforeseen situation;
   all parts of the apparatus upstream of the disconnecting means are disconnected as a whole from the parts downstream of said disconnecting means and the parts polluted by the sample, lodged in the container of said upstream part, are suitably disposed of and discharged after use as a whole, and
   the assembling and programming of the apparatus, the draw and the disposal of the polluted upstream parts and the recovery of the test tubes, are carried out in different moments and therefore can be carried out by different operators.

* * * * *